United States Patent
Dunshee et al.

[11] Patent Number: 5,976,117
[45] Date of Patent: Nov. 2, 1999

[54] WOUND DRESSING

[75] Inventors: Wayne K. Dunshee, Maplewood; Mary L. Brown, St. Paul, both of Minn.

[73] Assignee: 3M Innovative Properties Company, St. Paul, Minn.

[21] Appl. No.: 08/719,937

[22] Filed: Sep. 25, 1996

[51] Int. Cl.$^6$ .................................................. A61F 13/02
[52] U.S. Cl. ........................... 604/307; 604/304; 602/41; 602/43; 602/48
[58] Field of Search ............................... 602/41; 604/307, 604/304

[56] References Cited

U.S. PATENT DOCUMENTS

| | | | |
|---|---|---|---|
| 3,908,650 | 9/1975 | Dunshee et al. ........................ | 128/156 |
| 4,310,509 | 1/1982 | Berglund et al. ......................... | 424/28 |
| 4,323,557 | 4/1982 | Rosso et al. ............................... | 424/28 |
| 4,650,705 | 3/1987 | Ghodsian .................................. | 428/40 |
| 4,728,323 | 3/1988 | Matson ..................................... | 604/304 |
| 5,238,685 | 8/1993 | Wren ....................................... | 424/445 |
| 5,520,762 | 5/1996 | Rasmussen et al. ..................... | 156/216 |
| 5,653,699 | 8/1997 | Reed et al. .............................. | 604/307 |

FOREIGN PATENT DOCUMENTS

| | | |
|---|---|---|
| 0413251A1 | 2/1991 | European Pat. Off. . |
| 96/26251 | 8/1996 | WIPO . |
| 96/26253 | 8/1996 | WIPO . |

*Primary Examiner*—Richard J. Apley
*Assistant Examiner*—Kelvin Hart
*Attorney, Agent, or Firm*—Robert W. Sprague

[57] ABSTRACT

A flexible sheet material for covering wounds, comprising at least two regions. The first region is in contact with the wound, and facilitates healing of the wound. The second region surrounds the first region and comprises an antimicrobial agent to inhibit or prevent the migration of microorganisms from the external environment to the first region.

21 Claims, 1 Drawing Sheet

WOUND DRESSING

FIELD OF THE INVENTION

The present invention relates to a flexible sheet material for covering wounds. The flexible sheet material includes an antimicrobial agent.

BACKGROUND OF THE INVENTION

Various materials are commonly used to cover a wound while the wound heals. These materials provide a protective layer over the wound, facilitating healing in a moist environment while acting as a barrier to liquids and microorganisms.

In typical wound dressings, an absorbant material is held in place over the wound by a piece of tape. The absorbant material may or may not comprise a medicament. A typical wound dressing in which the absorbant material comprises a medicament is disclosed in U.S. Pat. No. 4,728,323 (Matson). These antimicrobial wound dressings are prepared by vapor coating or sputter etching certain silver salts onto a variety of wound dressing substrates.

Alternatively, the wound dressing may comprise a film or tape wherein a substantial portion of the film or tape is covered by an adhesive with an antimicrobial agent dispersed throughout or complexed to the adhesive. Such wound dressings are disclosed in U.S. Pat. No. 4,310,509 (Berglund, et al.) and U.S. Pat. No. 4,323,557 (Rosso, et al.), respectively.

SUMMARY OF THE INVENTION

The present invention provides a flexible sheet material having a plurality of edges and comprising a backing and a dermatologically acceptable pressure-sensitive adhesive covering at least a portion of the backing and for adhering the sheet material to skin, the sheet material being defined by at least two regions including:

a) a first region having a first surface opposite the backing adapted for contact with a wound and for facilitating cell regeneration in and therefore healing of the wound, the first region being removed from the edges of the flexible sheet material; and b) a second region substantially surrounding the first region and having a second surface opposite the backing, the second region comprising an antimicrobial agent available at the second surface in an amount which is greater than that which facilitates wound cell regeneration and is at least sufficient to inhibit or essentially prevent migration of microorganisms to the first region from the external environment along the interface between the sheet material and skin to which the sheet material has been adhered.

The first region preferably comprises cell growth-enhancing agents. The first region also preferably provides a void space for wound exudate. A wound often secretes fluids during the healing process, and this void space provides an area into which the wound exudate may flow.

The flexible sheet material of the invention may additionally include an intermediate region between the first and second regions. This intermediate region may simply comprise the uncoated backing of the flexible sheet material. Alternatively, a dermatologically acceptable pressure sensitive adhesive may be applied to the backing in the intermediate region, and this adhesive may or may not comprise an antimicrobial agent or a medicament of some type. If this intermediate region comprises the same antimicrobial agent as is in the second region, this antimicrobial agent will be present at a lower concentration than that of the second region.

BRIEF DESCRIPTION OF THE DRAWINGS

The invention will be more fully explained with reference to the following drawings in which.

Figure 1:
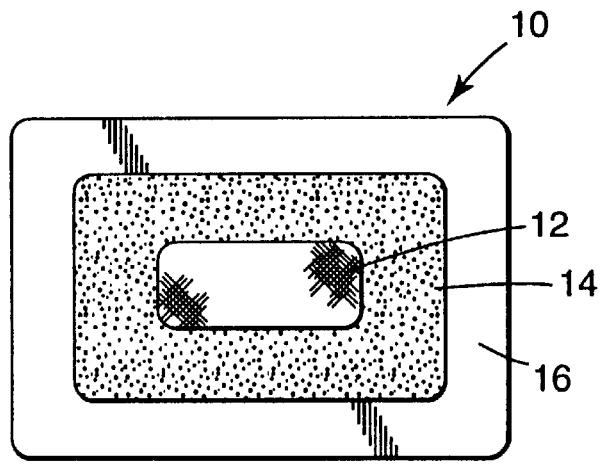
FIG. 1 is a top plan view of an illustrative embodiment of the invention.

These figures, which are idealized, are not to scale and are intended to be merely illustrative and non-limiting.

DETAILED DESCRIPTION OF PREFERRED EMBODIMENTS

Wound dressing 10 comprises backing 16, pressure-sensitive adhesive layer 14 coated on a portion of backing 16, and an absorbant web or other material 12 to provide a void space for wound exudate. The absorbant web or other material 12 is adhered to backing 16 by means of an adhesive which may or may not be an extension of adhesive layer 14. Adhesive layer 14 comprises an antimicrobial agent which is available at the surface of adhesive layer 14 to inhibit or essentially prevent migration of microorganisms from the external environment to web 12.

The first region of wound dressing 10 comprises web 12, and the portions of any adhesive layer and backing 16 directly underlying web 12. The exposed surface of web 12 is considered to be the first surface of the first region as defined in the instant claims.

The second region of wound dressing 10 comprises the portions of the adhesive layer 14 and backing 16 extending beyond and not underlying web 12. The exposed surface of adhesive layer 14 is considered to be the first surface of the second region as defined in the instant claims.

It may be desirable to include a barrier layer to inhibit or prevent any antimicrobial contained in the adhesive layer underlying web or other material 12 from migrating to the exposed surface of web or other material 12. Typically, the barrier, which is positioned between web or other material 12 and the underlying adhesive layer, comprises a polymeric film on the order of about 5 to 10 micrometers which is substantially impermeable to the antimicrobial agent.

Figure 2:
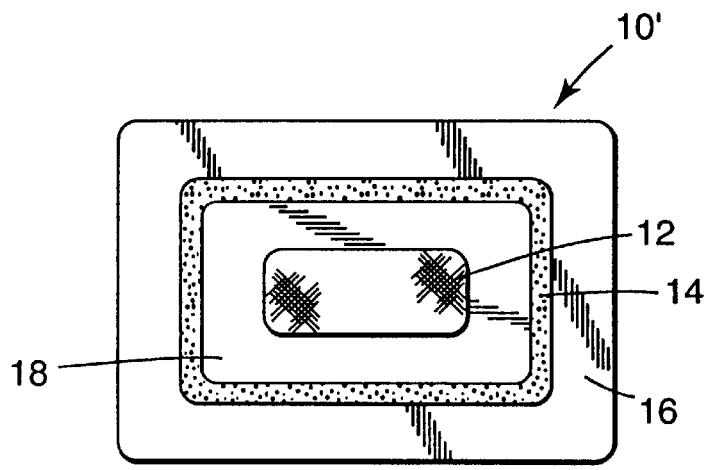
FIG. 2 is a top plan view of an alternative embodiment of the invention.

FIG. 2 illustrates a top plan view of an alternative embodiment 10' of the invention further comprising optional intermediate region 18.

Figure 3:
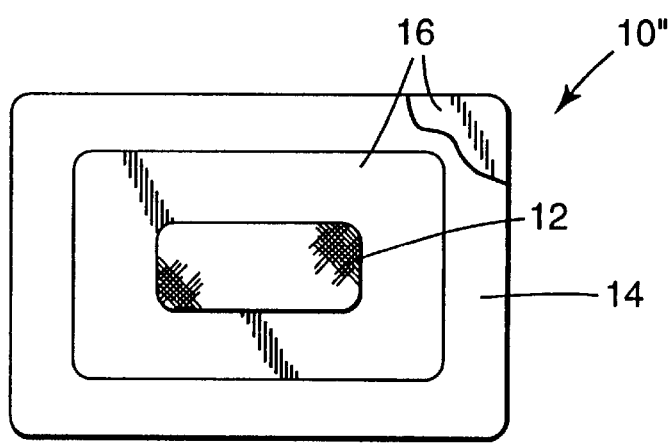
FIG. 3 is a partial breakaway view of an embodiment of the invention.

FIG. 3 depicts a partial breakaway view of an embodiment 10" of the invention. In this embodiment, second region 14 extends to the outer edge of the flexible sheet material.

The backing 16 is preferably flexible, yet possesses sufficient structural integrity to provide a durable wound dressing. The backing should not cause or contribute to the degradation of the adhesive. The backing is preferably permeable to air and moisture vapor. The backing is also preferably substantially impermeable to liquids and microorganisms.

Examples of suitable materials for backing include, but are not limited to, polyurethanes, polyesters, and vinyls. The preferred thickness of the backing will depend on which material is used and whether the backing is a solid film or a foam. Typical thicknesses range from about 10 micrometers for a thin film backing to about 800 micrometers for a foam backing.

The pressure sensitive adhesive used in the wound dressing of the invention should adhere well to skin, and be dermatologically acceptable. Additionally, the adhesive should be such as to allow the antimicrobial agent to be added thereto, without causing degradation of the antimicrobial agent. Typical adhesives used in the flexible sheet material of the invention may include, but are not limited to, acrylate adhesives, rubber-based adhesives, and silicone-based adhesives.

The combination of adhesive and backing should have a moisture vapor transmission rate of at least about 300 grams/m$^2$/24 hours, and more preferably a moisture vapor transmission rate of at least about 500 grams/m$^2$/24 hours.

The absorbant web or other material 12 present in the first region of the wound dressing preferably includes a material with substantial void space. Such a void space provides an area for the wound exudate to flow into. Examples of suitable materials include but are not limited to fibers of cotton, rayon, or other cellulosic materials, polyolefins, polyesters, and combinations thereof.

Additionally, absorbant web or other material 12 preferably comprises a mild antimicrobial, and/or cell growth enhancing agents, and/or other medicaments. Any antimicrobial agent present in the absorbant web or other material 12 is typically a mild antimicrobial, or the same antimicrobial agent as is in the second region but at a much lower concentration. Any antimicrobial and amount thereof selected for inclusion in absorbant web or other material 12 should be compatible for direct contact with a wound. Examples of other medicaments suitable for use in the absorbant web or other material 12 include but are not limited to fungicides, anti-acne agents, antioxidants, antibiotics, and cosmetic astringents.

Antimicrobial agents which may be present in pressure-sensitive adhesive layer 14 in the second region of wound dressing 10 include cosmetic biocides. Examples of suitable antimicrobial agents include but are not limited to iodine, hydrogen peroxide, benalkonium chloride, and aluminum chlorohydrate. One of ordinary skill in the art will readily be able to select an appropriate amount of the selected antimicrobial for inclusion in adhesive layer 14.

EXAMPLES

Example 1

A strip of 2.5×7.6 cm Microfoam™ Tape commercially available from 3M was cut. Then a 0.3 cm wide band of Ioban™ 2 6650 Antimicrobial Film commercially available from 3M was cut and applied to the outside edge of the adhesive on the Microfoam™ Tape. The liner was removed to expose the adhesive surface of the antimicrobial film. Then a 1.9×2.5 cm piece of 125.45 g/m$^2$, 90/10 polypropylene/rayon blend single side laminated with 530 P™ high density polyethylene netting (the entire construction commercially available from Applied Extrusion Technologies (AET), Middletown, Del.) was placed in the center of the adhesive side of the Microfoam™ Tape. A solution of Benzalkonium Chloride (BTC 50 USP) commercially available from Stepan Company, Northfield, Ill. (0.13% wt/wt in Ethanol/water) was added to the pad to a concentration of 0.13 wt/wt %.

Example 2

A strip of 4×10 cm piece of melt blown polyurethane tape commercially available from Medical Specialties Division of 3M Company may be cut. A 1 cm wide ring of PVP-Iodine™ 30/06 commercially available from BASF Corporation, Parsippany, N.J. (10% wt/wt in Ethanol) is then painted onto the adhesive side of the strip of melt blown polyurethane tape using a cotton swab. The ring is placed 0.6 cm inside of the outer perimeter of the piece of melt blown polyurethane tape. A 1×4 cm piece of 530 P™ high density polyethylene netting commercially available from Applied Extrusion Technologies (AET), Middletown, Del., that was vapor coated with silver chloride according to U.S. Pat. No. 4,728,323 is then placed inside the ring of PVP-Iodine at the center of the adhesive side of the piece of melt blown polyurethane tape.

Example 3

A 6.3×8.3 cm piece of Tegaderm™ HP Transparent Dressing commercially available from 3M was cut. Then a 1 cm ring of PVP stabilized Peroxide (PVP/02-1™) solution commercially available from ISP Technologies, Inc., Wayne, N.J. (5% wt/wt in Ethanol) was painted on using a cotton swab to the adhesive side of the tape. The ring was placed 0.6 cm inside the outer perimeter of the tape. A 2.5×2.5 cm pad of melt blown polypropylene was placed in the center of the adhesive side of the Tegaderm™ HP Transparent Dressing. A solution of Benzalkonium Chloride (BTC 50 USP) commercially available from Stepan Company, Northfield, Ill. (0.13% wt/wt in Ethanol/water) was added to the pad to a concentration of 0.13 wt/wt %.

Example 4

A 3×9 cm piece of Ioban™ 2 6650 Antimicrobial Film commercially available from 3M was cut. Then a 1.3 ×3.8 cm piece of 108.5 g/m$^2$, rayon double side laminated with 530 P high density polyethylene netting (the entire construction commercially available from Applied Extrusion Technologies (AET), Middletown, Del.) was placed in the center of the adhesive side of the antimicrobial film. A solution of Benzalkonium Chloride (BTC 50 USP) commercially available from Stepan Company, Northfield, Ill. (0.13% wt/wt in Ethanol/water) was added to the pad to a concentration of 0.13 wt/wt %.

Example 5

A 3×9 cm piece of Ioban™ 2 6650 Antimicrobial Film commercially available from 3M was cut. Then a 1.3 ×3.8 cm piece of 108.5 g/m$^2$, rayon double side laminated with 530 P high density polyethylene netting (the entire construction commercially available from Applied Extrusion Technologies (AET), Middletown, Del.), was placed in the center of the adhesive side of the antimicrobial film. A solution of PVP-Iodine™ 30/06 commercially available from BASF Corporation, Parsippany, N.J. (10% wt/wt in Ethanol) was added to the pad to a concentration of 10 wt/wt %.

Example 6

A 3×9 cm piece of Tegadermm Dressing commercially available from 3M was cut. Then a 1.3×3.8 cm piece of 108.5 g/m$^2$, rayon double side laminated with 530 P™ high density polyethylene netting (the entire construction commercially available from Applied Extrusion Technologies (AET), Middletown, Del.) was placed in the center of the adhesive side of the Tegaderm™ Dressing. Then a 1 cm ring of PVP Stabilized Peroxide (PVP/02-1™) solution commercially available from ISP Technologies, Inc., Wayne, N.J. (5% wt/wt in Ethanol) was painted on using a cotton swab to the adhesive side of the tape. The ring was around the perimeter of the pad. A solution of Benzalkonium Chloride (BTC 50 USP) commercially available from Stepan Company, Northfield, Ill. (0.13% wt/wt in Ethanol/water) was added to the pad to a concentration of 0.13 wt/wt %.

Example 7

A 3×9 cm piece of Tegaderm™ Dressing commercially available from 3M was cut. Then a 1.3×3.8 cm piece of 108.5 g/m², rayon double side laminated with 530 P™ high density polyethylene netting (the entire construction commercially available from Applied Extrusion Technologies (AET), Middletown, Del.), was placed in the center of the adhesive side of the Tegaderm™ Dressing. Then a 1 cm ring of PVP Stabilized Peroxide (PVP/02-1™) solution commercially available from ISP Technologies, Inc., Wayne, N.J. (5% wt/wt in Ethanol) was painted on using a cotton swab to the adhesive side of the tape. The ring was around the perimeter of the pad. A solution of PVP-Iodine™ 30/06 commercially available from BASF Corporation, Parsippany, N.J. (10% wt/wt in Ethanol) was added to the pad to a concentration of 10 wt/wt %.

What is claimed is:

1. A flexible sheet material having a plurality of edges and comprising a backing and a dermatologically acceptable pressure-sensitive adhesive covering at least a portion of said backing and for adhering said sheet material to skin, said sheet material being defined by at least three regions including:
   a) a first region having a first surface opposite said backing adapted for contact with a wound and for facilitating cell regeneration in and therefore healing of said wound, said first region being removed from said edges of said flexible sheet material;
   b) a second region substantially surrounding said first region and having a second surface opposite said backing, said second region comprising an antimicrobial agent available at said second surface in an amount which is greater than that which facilitates wound cell regeneration and is at least sufficient to inhibit or essentially prevent migration of microorganisms to said first region from the external environment along the interface between said sheet material and skin to which said sheet material has been adhered; and
   c) an intermediate region between said first region and said second region, wherein said intermediate region optionally comprises an antimicrobial agent, with the proviso that if the antimicrobial agent in said intermediate region is the same as that in the second region, then said antimicrobial agent is present in said intermediate region at a lower concentration than that of said second region.

2. The flexible sheet material of claim 1, wherein said first region includes a material providing a void space for wound exudate.

3. The flexible sheet material of claim 1, wherein said first surface of said first region is substantially free of said antimicrobial agent contained in said second region.

4. The flexible sheet material of claim 1, wherein said first region, said second region, and said intermediate region are substantially concentric.

5. The flexible sheet material of claim 2, wherein said first region comprises at least one agent compatible for direct wound contact.

6. The flexible sheet material of claim 5, wherein said agent is selected from the group consisting of a mild antimicrobial, a cell growth enhancing agent, and a medicament.

7. The flexible sheet material of claim 1, wherein said intermediate region is substantially free of said antimicrobial agent contained in said second region.

8. The flexible sheet material of claim 1, wherein said second region extends to said edges of said flexible sheet material.

9. The flexible sheet material of claim 1, wherein said second region comprises a pressure-sensitive adhesive comprising said antimicrobial agent dispersed throughout or complexed to said adhesive.

10. The flexible sheet material of claim 9, wherein said antimicrobial agent is selected from the group consisting of iodine, hydrogen peroxide, benzalkonium chloride, or aluminum chlorohydrate.

11. The flexible sheet material of claim 9, wherein said antimicrobial agent is iodine which is complexed to said pressure sensitive adhesive.

12. The flexible sheet material of claim 1, further comprising a release liner releasably adhered to said first and second surfaces.

13. The flexible sheet material of claim 1, in a substantially oval shape.

14. The flexible sheet material of claim 1, wherein the combination of said backing and said pressure sensitive adhesive exhibit a moisture vapor transmission rate greater than about 300 gms/m²/24 hour moisture vapor transmission rate.

15. The flexible sheet material of claim 1, wherein said backing is substantially impermeable to microorganisms, but is substantially permeable to moisture vapor.

16. The flexible sheet material of claim 1, wherein said backing is selected from the group consisting of a substantially breathable foam, a substantially waterproof film, and a non-woven material.

17. The flexible sheet material of claim 1, wherein said first region comprises a material with a void volume greater than about 25 percent.

18. The flexible sheet material of claim 17, wherein said material is a substantially porous netting.

19. The flexible sheet material of claim 1, wherein said first region comprises an absorbant material.

20. The flexible sheet material of claim 19, wherein said absorbant material is a non-woven fabric.

21. The flexible sheet material of claim 19, wherein said absorbant material is a woven fabric.

* * * * *